(12) United States Patent
Chenvainu et al.

(10) Patent No.: US 8,621,698 B2
(45) Date of Patent: Jan. 7, 2014

(54) TOOTHBRUSHES

(75) Inventors: Alexander T. Chenvainu, Sudbury, MA (US); Thomas A. Christman, Lexington, MA (US)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 13/080,699

(22) Filed: Apr. 6, 2011

(65) Prior Publication Data
US 2011/0179595 A1 Jul. 28, 2011

Related U.S. Application Data

(63) Continuation of application No. 10/666,497, filed on Sep. 19, 2003, now Pat. No. 7,941,886.

(51) Int. Cl.
*A61C 17/22* (2006.01)

(52) U.S. Cl.
USPC ............................ 15/22.1; 15/DIG. 5

(58) Field of Classification Search
USPC ....... 15/21.1, 22.1, 22.2, 22.4, 167.1, DIG. 5, 15/28
See application file for complete search history.

(56) References Cited

U.S. PATENT DOCUMENTS

| | | |
|---|---|---|
| 429,839 A | 6/1890 | Beissbarth |
| 601,405 A | 3/1898 | Shepherd |
| 819,444 A | 5/1906 | Monroe |
| 1,022,920 A | 4/1912 | Anderson |
| 1,063,523 A | 6/1913 | Farrar |
| 1,091,090 A | 3/1914 | Tacail |
| 1,142,698 A | 6/1915 | Grove et al. |
| 1,153,409 A | 9/1915 | Wheeler |
| 1,172,109 A | 2/1916 | Cammack |
| 1,188,134 A | 6/1916 | Arbat |
| 1,251,250 A | 12/1917 | Libby |
| 1,323,042 A | 11/1919 | Gardner |
| 1,544,404 A | 6/1925 | Hummel |
| 1,593,763 A | 7/1926 | Henderson |
| 1,673,638 A | 6/1928 | Peterson |
| 1,693,229 A | 11/1928 | Felmar |
| 1,698,128 A | 1/1929 | Funk |
| 1,753,290 A | 4/1930 | Graves |
| 1,758,632 A | 5/1930 | Wagner |
| 1,840,246 A | 1/1932 | Newman |
| 1,852,480 A | 4/1932 | Ruetz |
| 1,872,832 A | 8/1932 | Silverberg |

(Continued)

FOREIGN PATENT DOCUMENTS

| | | |
|---|---|---|
| AU | 4469693 | 6/1994 |
| BE | 894944 | 1/1983 |

(Continued)

OTHER PUBLICATIONS

U.S. Appl. No. 12/186,639, field Aug. 6, 2008, Braun et al.

(Continued)

*Primary Examiner* — Laura C Guidotti
(74) *Attorney, Agent, or Firm* — John P. Colbert

(57) ABSTRACT

Toothbrush heads, e.g., for power toothbrushes, are provided. The toothbrush heads include a support member and a plurality of bristles or tufts of bristles extending from the support member, the bristles or bristle tufts having different lengths. The contour of the bristles may be selected to allow substantially all of the bristles to contact the dentition during brushing.

7 Claims, 10 Drawing Sheets

(56) References Cited

U.S. PATENT DOCUMENTS

| | | | |
|---|---|---|---|
| 1,908,510 A | 5/1933 | Dodson |
| 2,043,898 A | 6/1936 | Malcolm |
| 2,139,245 A | 12/1938 | Ogden |
| 2,164,219 A | 6/1939 | McGerry |
| 2,172,624 A | 9/1939 | Gabriel et al. |
| 2,175,975 A | 10/1939 | Steiner |
| 2,139,249 A | 3/1940 | Flanders et al. |
| 2,220,053 A | 10/1940 | Pruner |
| 2,238,603 A | 4/1941 | Runnels |
| 2,266,195 A | 12/1941 | Lay |
| 2,328,998 A | 9/1943 | Radford |
| 2,486,203 A | 10/1949 | Pieper |
| 2,556,691 A | 6/1951 | Harshbarger |
| 2,583,886 A | 1/1952 | Schlegel |
| 2,628,377 A | 2/1953 | Cockriel |
| 2,637,870 A | 5/1953 | Cohen |
| 2,653,598 A | 9/1953 | Torino |
| 2,655,674 A | 10/1953 | Grover |
| 2,655,675 A | 10/1953 | Grover |
| 2,655,676 A | 10/1953 | Grover |
| 2,832,088 A | 4/1958 | Peilet et al. |
| 3,016,554 A | 1/1962 | Peterson |
| 3,082,457 A | 3/1963 | Lucibello et al. |
| 3,128,487 A | 4/1964 | Vallis |
| 3,133,546 A | 5/1964 | Dent |
| 3,159,859 A | 12/1964 | Rasmussen |
| 3,177,509 A | 4/1965 | Cyzer |
| 3,196,299 A * | 7/1965 | Kott ................... 310/81 |
| 3,230,562 A | 1/1966 | Birch |
| 3,295,156 A | 1/1967 | Brant |
| 3,302,230 A | 2/1967 | Poppelman |
| 3,327,339 A | 6/1967 | Lemelson |
| 3,386,118 A | 6/1968 | Morioka et al. |
| 3,398,421 A | 8/1968 | Rashbaum |
| 3,403,070 A | 9/1968 | Lewis, Jr. |
| 3,411,979 A | 11/1968 | Lewis |
| RE26,688 E | 10/1969 | Lemelson |
| 3,491,396 A | 1/1970 | Eannarino et al. |
| 3,613,143 A | 10/1971 | Muhler et al. |
| 3,683,442 A | 8/1972 | Holly |
| 3,742,608 A | 7/1973 | Jones |
| 3,903,906 A | 9/1975 | Collis |
| 3,984,890 A | 10/1976 | Collis |
| 4,033,008 A | 7/1977 | Warren et al. |
| 4,115,893 A | 9/1978 | Nakata et al. |
| 4,156,620 A | 5/1979 | Clemens |
| 4,167,794 A | 9/1979 | Pomeroy |
| 4,202,361 A | 5/1980 | Bills |
| 4,268,933 A | 5/1981 | Papas |
| 4,288,883 A | 9/1981 | Dolinsky |
| 4,317,463 A | 3/1982 | Massetti |
| 4,356,585 A | 11/1982 | Protell et al. |
| 4,373,541 A | 2/1983 | Nishioka |
| 4,391,951 A | 7/1983 | Scheetz |
| 4,403,623 A | 9/1983 | Mark |
| 4,409,701 A | 10/1983 | Perches |
| 4,428,091 A | 1/1984 | Janssen |
| 4,429,434 A | 2/1984 | Sung-Shan |
| 4,476,280 A | 10/1984 | Poppe et al. |
| 4,480,351 A | 11/1984 | Koffler |
| 4,517,701 A | 5/1985 | Stanford, Jr. |
| 4,525,531 A | 6/1985 | Zukosky et al. |
| 4,534,081 A | 8/1985 | Spademan |
| 4,545,087 A | 10/1985 | Nahum |
| 4,573,920 A | 3/1986 | D'Argembeau |
| 4,585,795 A | 4/1986 | Linderborg |
| 4,603,166 A | 7/1986 | Poppe et al. |
| 4,616,064 A | 10/1986 | Zukosky et al. |
| 4,617,342 A | 10/1986 | Poppe et al. |
| 4,617,694 A | 10/1986 | Bori |
| 4,623,495 A | 11/1986 | Degoix et al. |
| 4,654,922 A | 4/1987 | Chen |
| 4,672,706 A | 6/1987 | Hill |
| 4,691,405 A | 9/1987 | Reed |
| 4,706,322 A | 11/1987 | Nicolas |
| 4,744,350 A | 5/1988 | Sato |
| 4,783,874 A | 11/1988 | Perches et al. |
| 4,802,255 A | 2/1989 | Breuer et al. |
| 4,833,194 A | 5/1989 | Kuan et al. |
| 4,841,761 A | 6/1989 | Stoy et al. |
| 4,852,202 A | 8/1989 | Ledwitz |
| 4,882,803 A | 11/1989 | Rogers et al. |
| 4,892,698 A | 1/1990 | Weihrauch |
| 4,894,880 A | 1/1990 | Aznavoorian |
| 4,913,133 A | 4/1990 | Tichy |
| 4,979,256 A | 12/1990 | Branford |
| 4,979,782 A | 12/1990 | Weihrauch |
| 4,989,287 A | 2/1991 | Scherer |
| 4,991,249 A | 2/1991 | Suroff |
| 5,020,179 A | 6/1991 | Scherer |
| 5,021,475 A | 6/1991 | Isayev |
| 5,034,450 A | 7/1991 | Betz et al. |
| D325,821 S | 5/1992 | Schwartz |
| 5,114,214 A | 5/1992 | Barman |
| 5,120,225 A | 6/1992 | Amit |
| 5,142,724 A | 9/1992 | Park |
| 5,165,131 A | 11/1992 | Staar |
| 5,184,368 A | 2/1993 | Holland |
| 5,186,627 A | 2/1993 | Amit et al. |
| 5,226,197 A | 7/1993 | Nack et al. |
| 5,228,116 A | 7/1993 | Harris et al. |
| 5,249,327 A | 10/1993 | Hing |
| D345,054 S | 3/1994 | Spence, Jr. |
| 5,291,878 A | 3/1994 | Lombardo et al. |
| 5,313,909 A | 5/1994 | Tseng et al. |
| 5,318,352 A | 6/1994 | Holland |
| 5,321,726 A | 6/1994 | Kafadar |
| 5,325,560 A | 7/1994 | Pavone et al. |
| 5,342,284 A | 8/1994 | Lemon et al. |
| D350,851 S | 9/1994 | Spence, Jr. |
| 5,350,248 A | 9/1994 | Chen |
| 5,392,483 A * | 2/1995 | Heinzelman et al. ........ 15/167.1 |
| 5,407,254 A | 4/1995 | Hegemann |
| 5,421,726 A | 6/1995 | Okada |
| 5,458,400 A | 10/1995 | Meyer |
| 5,476,384 A | 12/1995 | Giuliani et al. |
| 5,524,319 A | 6/1996 | Avidor |
| 5,535,474 A | 7/1996 | Salazar |
| 5,546,626 A | 8/1996 | Chung |
| 5,590,434 A | 1/1997 | Imai |
| 5,593,213 A | 1/1997 | Meessmann |
| 5,604,951 A | 2/1997 | Shipp |
| 5,623,746 A | 4/1997 | Ichiro |
| 5,628,082 A * | 5/1997 | Moskovich ................... 15/110 |
| 5,651,157 A | 7/1997 | Hahn |
| 5,655,249 A | 8/1997 | Li |
| 5,658,148 A | 8/1997 | Neuberger et al. |
| 5,660,546 A | 8/1997 | Shafer |
| 5,678,275 A | 10/1997 | Derfner |
| D386,617 S | 11/1997 | Shyu |
| 5,706,542 A | 1/1998 | Okada |
| 5,722,106 A | 3/1998 | Masterman et al. |
| 5,723,543 A | 3/1998 | Modic |
| 5,742,972 A | 4/1998 | Bredall et al. |
| 5,778,474 A | 7/1998 | Shek |
| 5,791,007 A | 8/1998 | Tsai |
| 5,799,354 A | 9/1998 | Amir |
| 5,802,656 A * | 9/1998 | Dawson et al. ................. 15/110 |
| 5,823,633 A | 10/1998 | Weihrauch |
| D401,414 S | 11/1998 | Vrignaud |
| 5,842,249 A | 12/1998 | Sato |
| 5,864,915 A | 2/1999 | Ra |
| 5,946,759 A | 9/1999 | Cann |
| 5,946,789 A | 9/1999 | Junkers |
| 5,974,619 A | 11/1999 | Weihrauch |
| 5,987,681 A | 11/1999 | Hahn et al. |
| 6,006,394 A | 12/1999 | Bredall et al. |
| 6,018,840 A | 2/2000 | Guay et al. |
| 6,035,476 A | 3/2000 | Underwood et al. |
| 6,041,467 A | 3/2000 | Roberts et al. |
| 6,041,468 A | 3/2000 | Chen et al. |
| 6,088,870 A | 7/2000 | Hohlbein |
| 6,108,851 A | 8/2000 | Bredall et al. |
| 6,112,361 A | 9/2000 | Brice |

(56) References Cited

U.S. PATENT DOCUMENTS

| | | | |
|---|---|---|---|
| 6,148,310 A | 11/2000 | Azagury et al. | |
| 6,151,745 A | 11/2000 | Roberts et al. | |
| 6,161,245 A | 12/2000 | Weihrauch | |
| 6,178,582 B1 | 1/2001 | Halm | |
| 6,199,242 B1 | 3/2001 | Masterman et al. | |
| 6,202,241 B1 | 3/2001 | Hassell et al. | |
| D440,048 S | 4/2001 | Beals et al. | |
| 6,209,164 B1 | 4/2001 | Sato | |
| 6,237,178 B1 | 5/2001 | Krammer et al. | |
| D443,985 S | 6/2001 | Beals et al. | |
| D444,629 S * | 7/2001 | Etter et al. | D4/130 |
| 6,253,404 B1 | 7/2001 | Boland et al. | |
| 6,286,173 B1 | 9/2001 | Briones | |
| 6,290,302 B1 | 9/2001 | Boucherie | |
| 6,298,513 B1 | 10/2001 | Rief et al. | |
| 6,308,367 B1 | 10/2001 | Beals et al. | |
| 6,363,565 B1 | 4/2002 | Paffrath | |
| 6,389,634 B1 | 5/2002 | Devlin et al. | |
| 6,391,445 B1 | 5/2002 | Weihrauch | |
| 6,405,401 B1 | 6/2002 | Hellerud et al. | |
| 6,421,865 B1 | 7/2002 | McDougall | |
| 6,453,497 B1 | 9/2002 | Chiang et al. | |
| 6,477,729 B1 | 11/2002 | Ben-Ari | |
| 6,553,604 B1 | 4/2003 | Braun et al. | |
| 6,701,565 B2 | 3/2004 | Hafemann | |
| 6,725,490 B2 | 4/2004 | Blaustein et al. | |
| 6,776,597 B2 | 8/2004 | Buhler | |
| 6,807,703 B2 | 10/2004 | Van Gelder et al. | |
| 6,826,797 B1 | 12/2004 | Chenvainu et al. | |
| 6,889,401 B2 | 5/2005 | Fattor et al. | |
| 6,892,412 B2 | 5/2005 | Gatzemeyer et al. | |
| 6,892,413 B2 | 5/2005 | Blaustein et al. | |
| 6,918,154 B2 | 7/2005 | Ben-Ari | |
| 6,931,688 B2 | 8/2005 | Moskovich et al. | |
| 6,938,294 B2 | 9/2005 | Fattor et al. | |
| 6,983,507 B2 | 1/2006 | McDougall | |
| 6,988,777 B2 | 1/2006 | Pfenniger et al. | |
| 6,993,804 B1 | 2/2006 | Braun et al. | |
| 7,008,225 B2 | 3/2006 | Ito et al. | |
| 7,160,508 B2 | 1/2007 | Lee | |
| 7,222,381 B2 | 5/2007 | Kraemer | |
| 7,225,494 B2 | 6/2007 | Chan | |
| 7,251,849 B2 | 8/2007 | Moskovich | |
| 7,392,562 B2 | 7/2008 | Boland et al. | |
| 7,494,566 B2 | 2/2009 | Carroll | |
| 7,934,284 B2 * | 5/2011 | Braun et al. | 15/22.1 |
| 2001/0007161 A1 | 7/2001 | Masterman et al. | |
| 2001/0013151 A1 | 8/2001 | Gelder et al. | |
| 2001/0020314 A1 | 9/2001 | Calabrese | |
| 2002/0004964 A1 | 1/2002 | Luchino et al. | |
| 2002/0084550 A1 | 7/2002 | Roberts et al. | |
| 2002/0192621 A1 | 12/2002 | Ben-Ari | |
| 2003/0041402 A1 | 3/2003 | Stein | |
| 2003/0066147 A1 | 4/2003 | Roh | |
| 2003/0079304 A1 | 5/2003 | Dworzan | |
| 2003/0084525 A1 | 5/2003 | Blaustein | |
| 2003/0084528 A1 | 5/2003 | Chan | |
| 2003/0084533 A1 | 5/2003 | Gelder et al. | |
| 2003/0159224 A1 | 8/2003 | Fischer et al. | |
| 2004/0016067 A1 | 1/2004 | Kraemer | |
| 2004/0060136 A1 | 4/2004 | Gatzemeyer | |
| 2004/0068809 A1 | 4/2004 | Weng | |
| 2004/0083566 A1 | 5/2004 | Blaustein et al. | |
| 2004/0084063 A1 | 5/2004 | Vago | |
| 2004/0123409 A1 | 7/2004 | Dickie | |
| 2004/0128784 A1 | 7/2004 | Ben-Ari | |
| 2004/0177458 A1 | 9/2004 | Chan | |
| 2004/0177462 A1 * | 9/2004 | Brown et al. | 15/167.1 |
| 2004/0255416 A1 * | 12/2004 | Hohlbein | 15/106 |
| 2004/0261203 A1 | 12/2004 | Dworzan | |
| 2005/0060822 A1 | 3/2005 | Chenvainu et al. | |
| 2005/0235439 A1 | 10/2005 | Braun et al. | |
| 2005/0273961 A1 | 12/2005 | Moskovich et al. | |
| 2006/0272112 A9 | 12/2006 | Braun et al. | |
| 2007/0251040 A1 | 11/2007 | Braun et al. | |
| 2008/0060155 A1 | 3/2008 | Braun et al. | |
| 2008/0178401 A1 | 7/2008 | Claire-Zimmet et al. | |
| 2009/0172900 A1 | 7/2009 | Brown, Jr. et al. | |
| 2010/0162499 A1 | 7/2010 | Braun et al. | |

FOREIGN PATENT DOCUMENTS

| | | |
|---|---|---|
| CA | 454913 | 3/1949 |
| CA | 2483825 | 10/2004 |
| CH | 103 194 | 1/1924 |
| CH | 169 312 | 5/1934 |
| CH | 609238 | 2/1979 |
| CN | 2119280 U | 10/1992 |
| DE | 558 852 | 9/1932 |
| DE | 571724 | 3/1933 |
| DE | 813 990 | 7/1949 |
| DE | 1112966 | 8/1961 |
| DE | 1 883 020 | 11/1963 |
| DE | 7343826 U | 11/1974 |
| DE | 75 33 143 U | 2/1976 |
| DE | 25 00132 | 7/1976 |
| DE | 25 46 712 A | 4/1977 |
| DE | 25 46 712 A1 | 4/1977 |
| DE | 3621815 | 10/1978 |
| DE | 82 15 26637 U1 | 9/1982 |
| DE | 35 29 953 A1 | 3/1987 |
| DE | 36 07 200 A1 | 9/1987 |
| DE | 27 15414 | 1/1988 |
| DE | 37 44 630 A1 | 7/1989 |
| DE | 42 07 968 | 9/1993 |
| DE | 94 00 231.2 U1 | 3/1994 |
| DE | 44 12 301 | 10/1995 |
| DE | 29919053 | 12/2000 |
| DE | 100 28 530 A1 | 12/2001 |
| DK | 0076598 | 11/1953 |
| EP | 0 189 816 A2 | 8/1986 |
| EP | 360766 | 9/1988 |
| EP | 0322562 | 5/1989 |
| EP | 0 520 985 B1 | 9/1991 |
| EP | 0 704 179 A1 | 4/1996 |
| EP | 1004282 | 5/2000 |
| EP | 0 783 850 B1 | 3/2001 |
| EP | 0 870 440 B1 | 12/2001 |
| EP | 1 320 309 A | 6/2003 |
| EP | 1 449 496 B1 | 9/2008 |
| FR | 459 442 | 11/1913 |
| FR | 829086 | 10/1938 |
| FR | 1075171 | 10/1954 |
| FR | 1 300 138 | 4/1961 |
| FR | 2541100 | 8/1984 |
| FR | 2548528 | 1/1985 |
| FR | 2559361 | 8/1985 |
| FR | 2 612 751 | 9/1988 |
| FR | 2 616 306 | 12/1988 |
| FR | 2789887 | 8/1999 |
| FR | 2 789 887 | 8/2000 |
| GB | 193 601 A | 3/1923 |
| GB | 280 067 A | 11/1927 |
| GB | 378 129 A | 8/1932 |
| GB | 490 892 A | 8/1938 |
| GB | 690 422 A | 4/1953 |
| GB | 1 164 597 A | 9/1969 |
| GB | 1 325 860 A | 8/1973 |
| GB | 1 537 526 | 12/1978 |
| GB | 2137080 | 10/1984 |
| GB | 2214420 | 6/1989 |
| GB | 2 214 420 A | 9/1989 |
| GB | 2247297 | 2/1992 |
| GB | 2 354 432 A | 3/2001 |
| JP | 50-11769 | 2/1975 |
| JP | 51-056165 U | 5/1976 |
| JP | 52-125962 U | 9/1977 |
| JP | 55-122633 U | 9/1980 |
| JP | 58-091931 U | 6/1983 |
| JP | 59-066433 U | 5/1984 |
| JP | 61-090877 | 5/1986 |
| JP | 61-187531 U | 11/1986 |
| JP | 63-066928 U | 5/1988 |
| JP | 2-119031 | 4/1990 |

(56) References Cited

FOREIGN PATENT DOCUMENTS

| | | |
|---|---|---|
| JP | 2-180203 | 7/1990 |
| JP | 3-3226 | 1/1991 |
| JP | 3-312978 | 9/1991 |
| JP | 4-123121 | 11/1992 |
| JP | 4-128627 | 11/1992 |
| JP | 5-69342 | 3/1993 |
| JP | 5-076416 | 3/1993 |
| JP | 05096597 | 4/1993 |
| JP | 5-123222 | 5/1993 |
| JP | 6-327517 A2 | 11/1994 |
| JP | 8103326 | 4/1996 |
| JP | 8103332 | 4/1996 |
| JP | 8257043 | 8/1996 |
| JP | 8299372 | 11/1996 |
| JP | 9-140456 | 3/1997 |
| JP | 9-187319 A2 | 7/1997 |
| JP | 2001-190333 | 7/2001 |
| JP | 2001-507360 | 7/2001 |
| JP | 2002-010832 | 1/2002 |
| JP | 2002-248118 | 9/2002 |
| JP | 2003-061986 | 3/2003 |
| JP | 2003-093415 | 4/2003 |
| JP | 2003-164473 | 6/2003 |
| RU | 2045216 | 10/1995 |
| RU | 2100001 C | 12/1997 |
| SU | 1687243 | 10/1991 |
| WO | WO 91/05088 | 4/1991 |
| WO | WO 92/04589 | 3/1992 |
| WO | WO 93/24034 | 12/1993 |
| WO | WO 95/01113 A1 | 1/1995 |
| WO | WO 96/23431 | 8/1996 |
| WO | WO 96/28994 | 9/1996 |
| WO | WO 97/14330 | 4/1997 |
| WO | WO 98/01055 | 1/1998 |
| WO | WO 00/21406 | 4/2000 |
| WO | WO 00/30495 | 6/2000 |
| WO | WO 00/34022 | 6/2000 |
| WO | WO 00/47083 | 8/2000 |
| WO | WO 00/64307 | 11/2000 |
| WO | WO 01/06947 A1 | 1/2001 |
| WO | WO 01/06946 A1 | 2/2001 |
| WO | WO 01/21036 | 3/2001 |
| WO | WO 01/43584 A1 * | 6/2001 |
| WO | WO 01/43586 | 6/2001 |
| WO | WO 01/89344 | 11/2001 |
| WO | WO 02/05679 A1 | 1/2002 |
| WO | WO 02/19942 A1 | 3/2002 |
| WO | WO 02/45617 | 6/2002 |

OTHER PUBLICATIONS

Board Opinion from the Chinese Patent Office with regard to Application No. 01806615.1 dated Jul. 17, 2007 with translation.
Office Action for U.S. Appl. No. 10/389,448 dated Feb. 25, 2009; Braun et al.; filed Mar. 14, 2003.
Office Action for U.S. Appl. No. 10/389,448 dated Jun. 2, 2006; Braun et al.; filed Mar. 14, 2003.
Office Action for U.S. Appl. No. 10/389,448 dated Oct. 26, 2007; Braun et al.; filed Mar. 14, 2003.
Office Action for U.S. Appl. No. 10/389,448 dated Jul. 2, 2008; Braun et al.; filed Mar. 14, 2003.
Office Action for U.S. Appl. No. 10/389,448 dated Apr. 4, 2008; Braun et al.; filed Mar. 14, 2003.
Office Action for U.S. Appl. No. 10/389,448 dated Feb. 22, 2007; Braun et al.; filed Mar. 14, 2003.
Office Action for U.S. Appl. No. 11/825,387 dated Feb. 19, 2010; Braun et al.; filed Jun. 22, 2010.
Office Action for U.S. Appl. No. 11/825,387 dated Feb. 19, 2010; Braun et al.; filed Jul. 6, 2007.
Office Action for U.S. Appl. No. 11/825,387 dated Feb. 11, 2009; Braun et al.; filed Jul. 6, 2007.
Office Action for U.S. Appl. No. 11/825,387 dated Aug. 29, 2008; Braun et al.; filed Jul. 6, 2007.
Office Action for U.S. Appl. No. 11/825,387 dated Dec. 6, 2007; Braun et al.; filed Jul. 6, 2007.
Office Action for U.S. Appl. No. 12/186,639 dated Jun. 22, 2010; Braun et al.; filed Aug. 6, 2008.
Office Action for U.S. Appl. No. 12/186,639 dated Dec. 23, 2009; Braun et al.; filed Aug. 6, 2008.
Office Action for U.S. Appl. No. 12/186,639 dated Aug. 6, 2008; Braun et al.; filed Aug. 6, 2008.
Office Action for U.S. Appl. No. 12/186,639 dated Sep. 2, 2010; Braun et al.; filed Aug. 6, 2008.
Office Action for U.S. Appl. No. 10/830,693 dated Feb. 26, 2009; Masterman et al.; filed Apr. 23, 2004.
Distinctive Plastics—Multi-Component Molding htip://www.distinctiveplastics.com/html/?id=2 copyright 2006.
Office Action for U.S. Appl. No. 10/830,693 dated Jul. 2, 2008; Masterman et al.; filed Apr. 23, 2004.
Office Action for U.S. Appl. No. 10/830,693 dated Mar. 3, 2008; Masterman et al.; filed Apr. 23, 2004.
Office Action for U.S. Appl. No. 10/830,693 dated Oct. 24, 2007; Masterman et al.; filing date Apr. 23, 2004.
Office Action for U.S. Appl. No. 10/830,693 dated May 15, 2007; Masterman et al.; filing date Apr. 23, 2004.
Office Action for U.S. Appl. No. 10/830,693 dated Aug. 17, 2006; Masterman et al.; filing date Apr. 23, 2004.
Office Action for U.S. Appl. No. 10/799,793 dated Jun. 19, 2009; Braun et al.; filing date May 2, 2007.
Office Action for U.S. Appl. No. 10/799,793 dated Apr. 25, 2008; Braun et al.; filing date May 2, 2007.
Office Action for U.S. Appl. No. 10/799,793 dated Mar. 12, 2004; Braun et al.; filing date May 2, 2007.
Office Action for U.S. Appl. No. 10/799,793 dated Apr. 18, 2007; Braun et al.; filing date May 2, 2007.
Office Action for U.S. Appl. No. 10/799,793 dated Dec. 27, 2007; Braun et al.; filing date May 2, 2007.
Office Action for U.S. Appl. No. 10/820,562 dated Jun. 22, 2010; Braun et al.; filing date Mar. 16, 2000.
Office Action for U.S. Appl. No. 10/820,562 dated Dec. 2, 2008; Braun et al.; filing date Mar. 16, 2000.
Office Action for U.S. Appl. No. 10/820,562 dated Jul. 27, 2009; Braun et al.; filing date Mar. 16, 2000.
Office Action for U.S. Appl. No. 10/820,562 dated Jul. 5, 2007; Braun et al.; filing date Mar. 16, 2000.
Office Action for U.S. Appl. No. 10/820,562 dated May 8, 2006; Braun et al.; filing date Mar. 16, 2000.
Office Action for U.S. Appl. No. 10/820,562 dated Aug. 15, 2005; Braun et al.; filing date Mar. 16, 2000.
Office Action for U.S. Appl. No. 10/389,448 dated Jun. 2, 2006; Braun et al.; filing date Mar. 14, 2003.
Office Action for U.S. Appl. No. 10/389,448 dated Oct. 26, 2007; Braun et al.; filing date Mar. 14, 2003.
Office Action for U.S. Appl. No. 10/389,448 dated Jul. 2, 2008; Braun et al.; filing date Mar. 14, 2003.
Office Action for U.S. Appl. No. 09/421,747 dated Jul. 16, 2001; Devlin et al., filing Oct. 20, 1999.
Office Action for U.S. Appl. No. 09/421,747 dated Nov. 9, 2001; Devlin et al., filing dateOct. 20, 1999.
Office Action for U.S. Appl. No. 09/421,747 dated Jan. 7, 2002; Devlin et al., filing date Oct. 20, 1999.
Office Actions for U.S.S. N. 09/573,576 from Jan. 29, 2003 to Sep. 17, 2004 from Chenvainu et al.
Office Actions for U.S. Appl. No. 09/634,087 from Jun. 24, 2003 to Aug. 17, 2005 Braun et al.
European Search Report.
European Search Report dated Jul. 24, 2009.
International Search Report.
Office Action for U.S. Appl. No. 08/887,866 dated Oct. 13, 1999; Roberts, filing date Jul. 3, 1997.
Office Action for U.S. Appl. No. 08/887,866 dated Mar. 26, 1999; Roberts, filing date Jul. 3, 1997.
Office Action for U.S. Appl. No. 08/887,866 dated Sep. 17, 1999; Roberts, filing date Jul. 3, 1997.

* cited by examiner

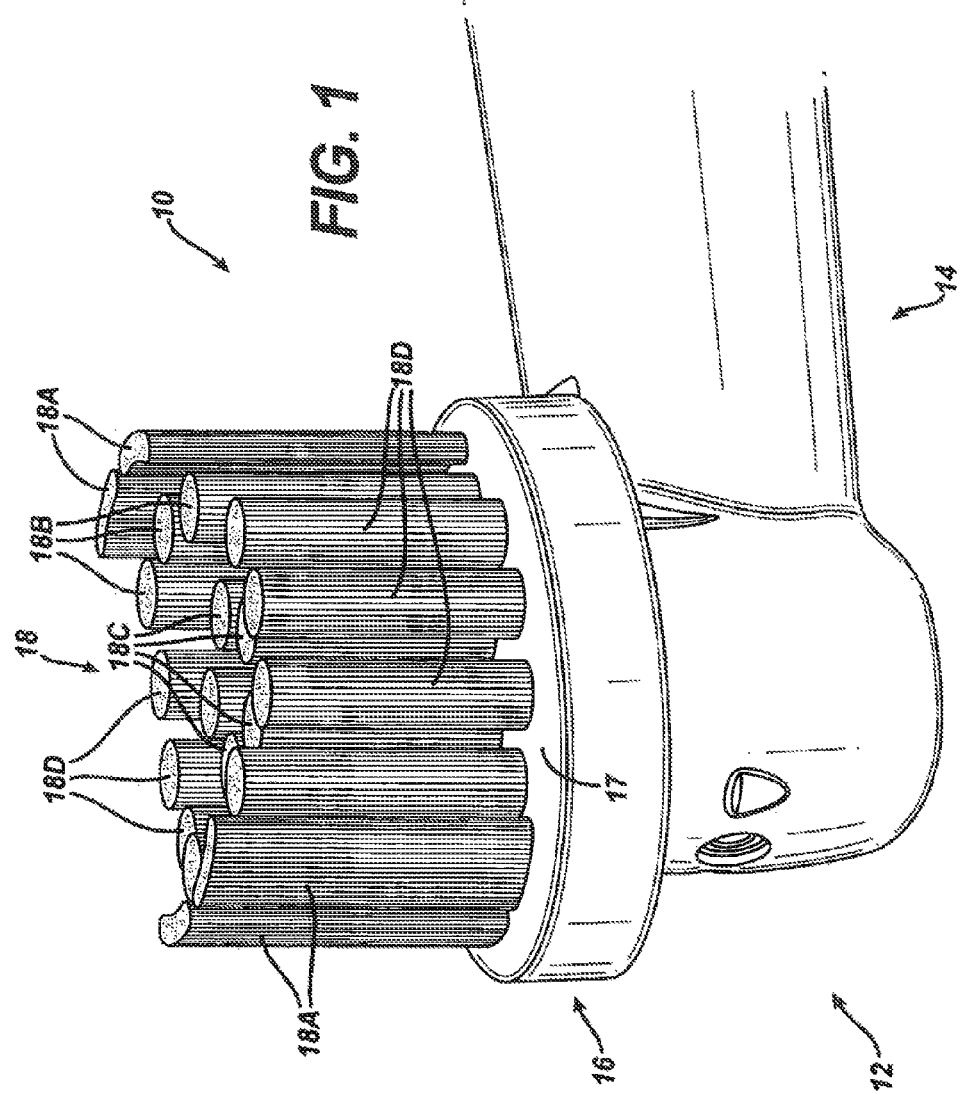

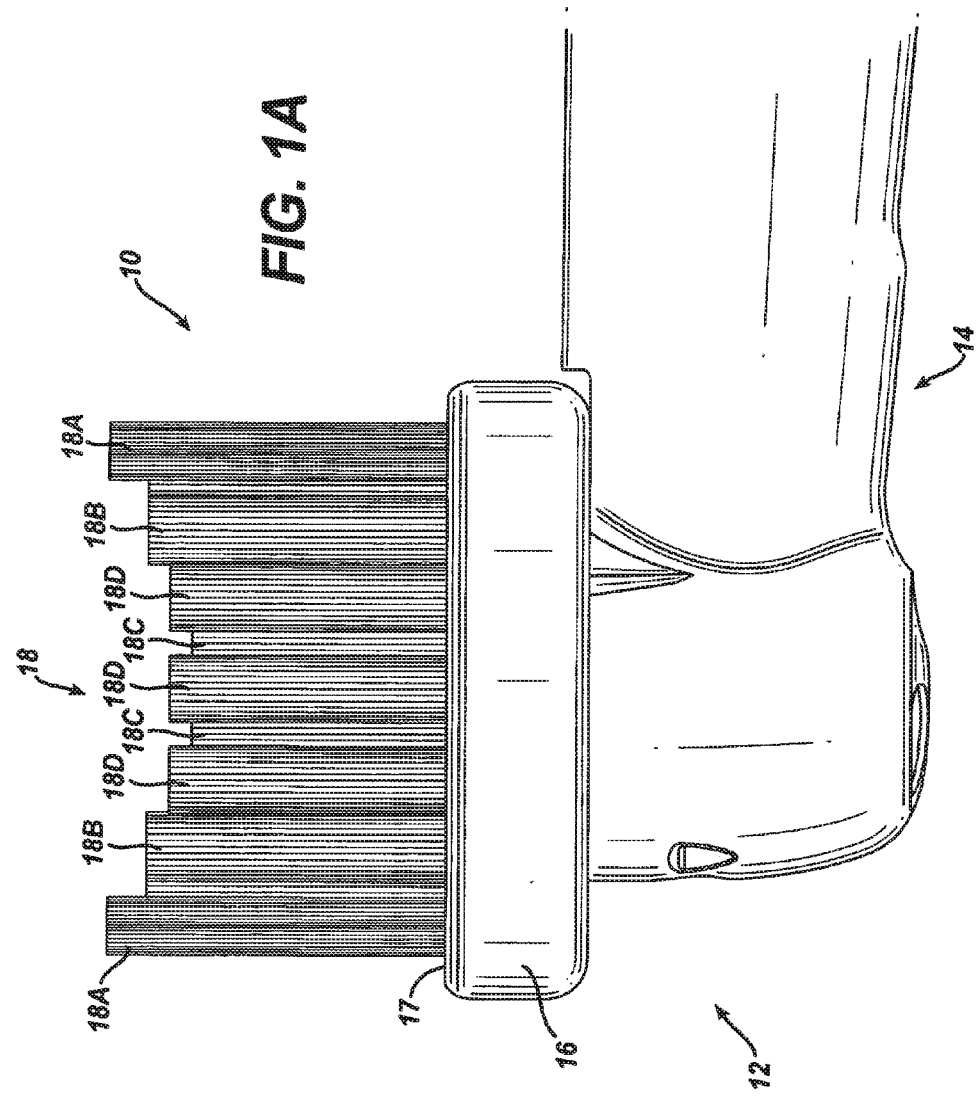

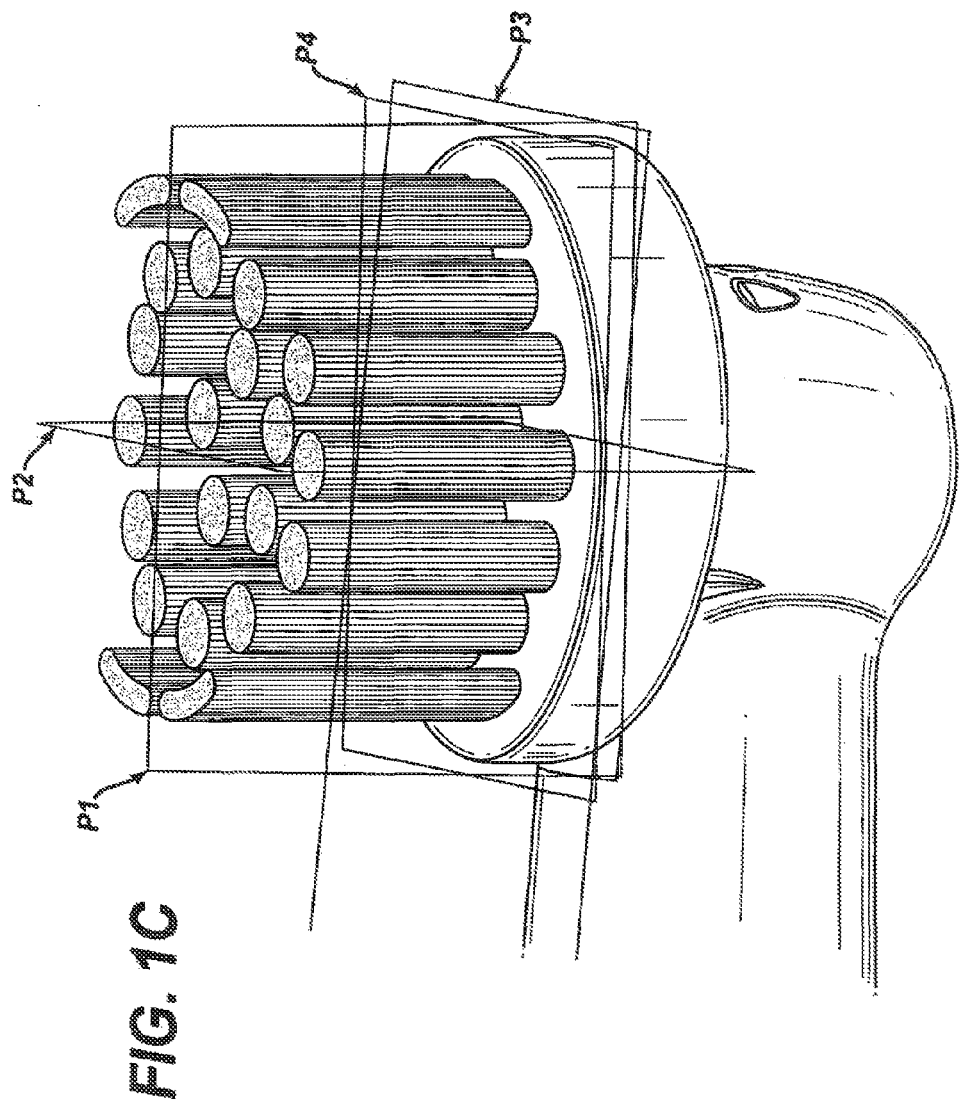

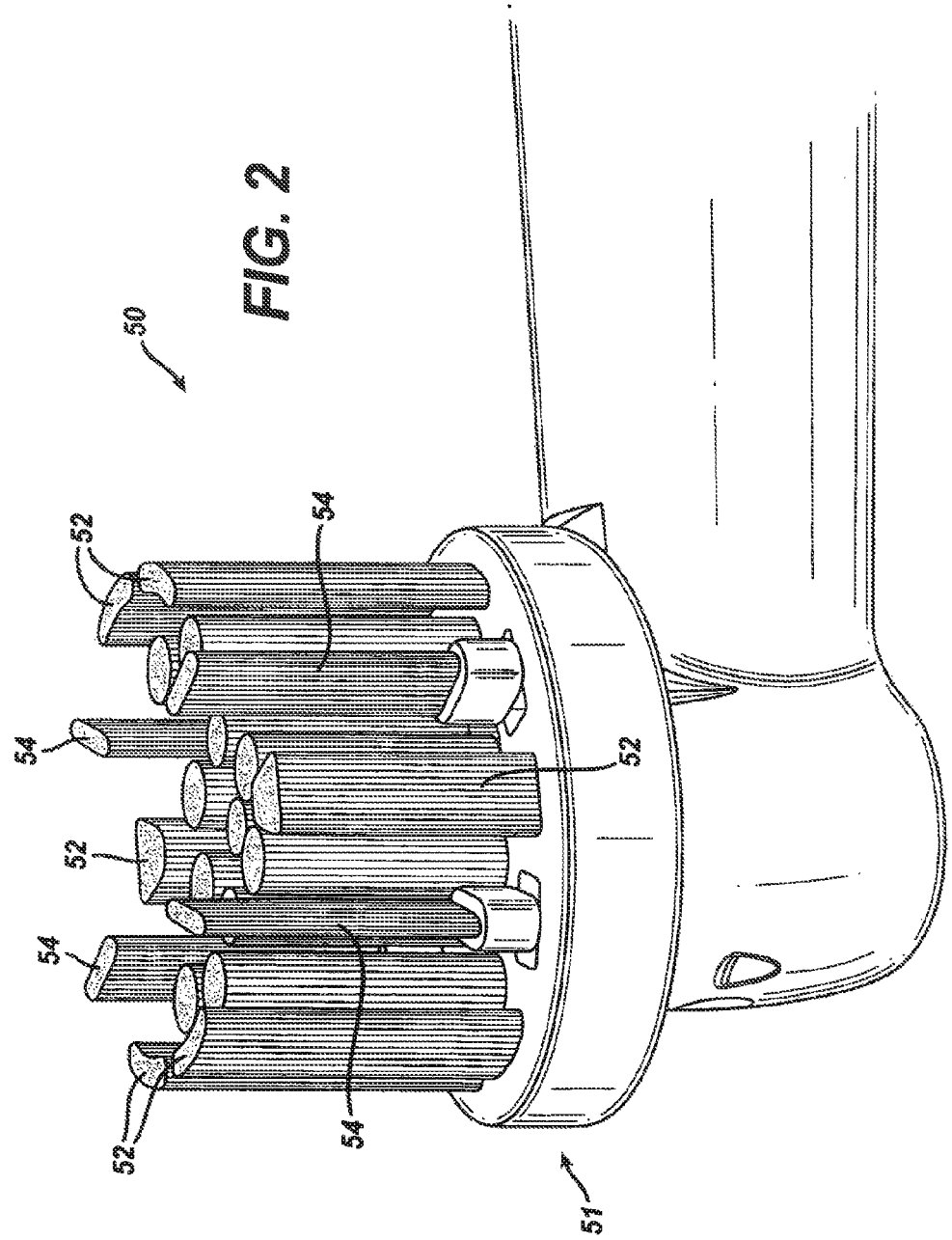

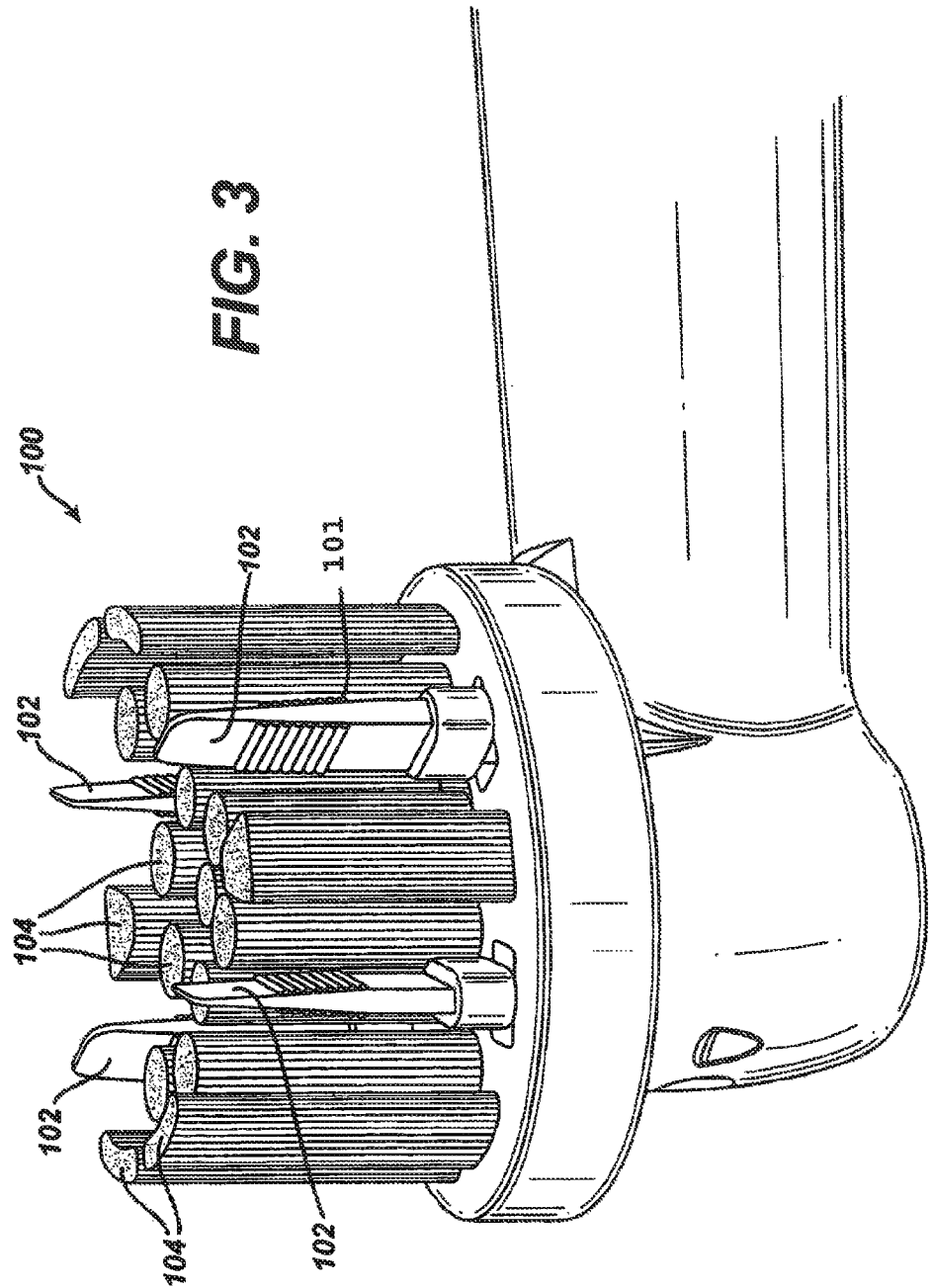

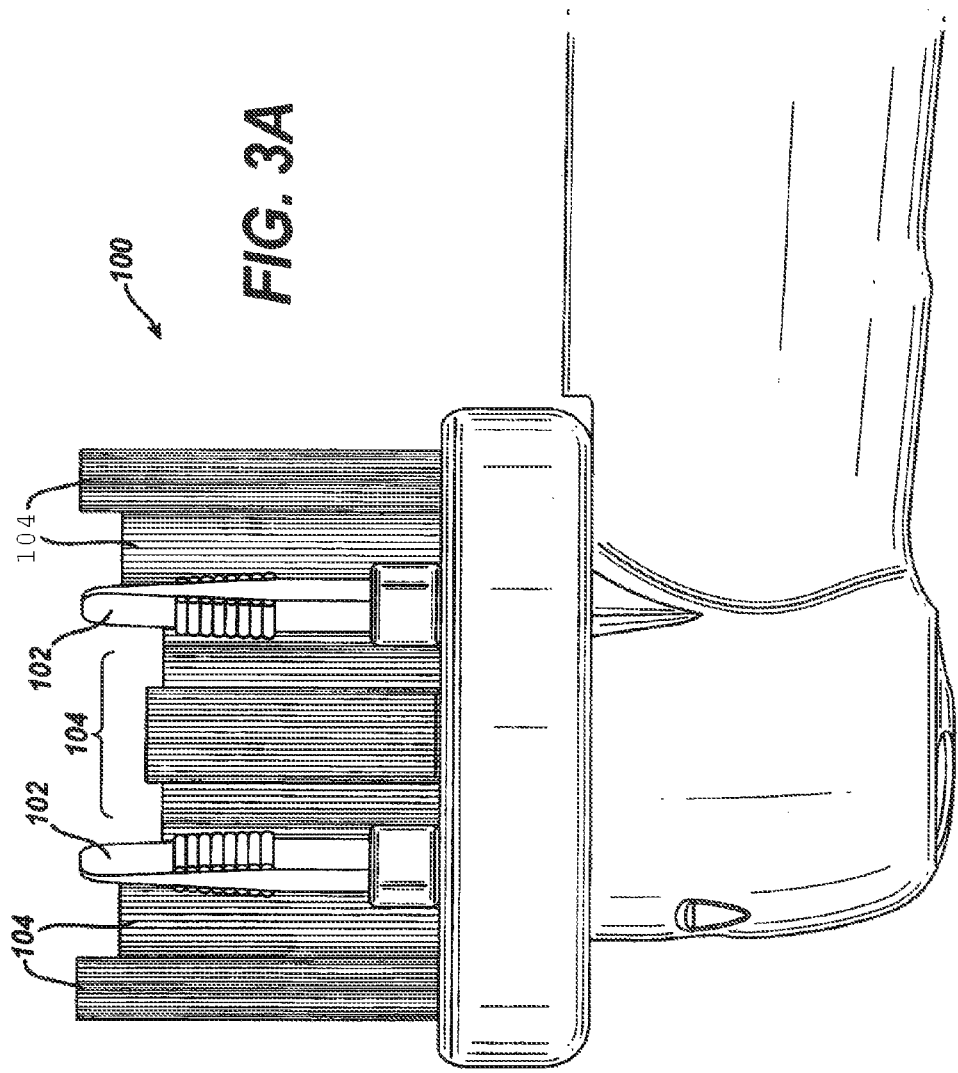

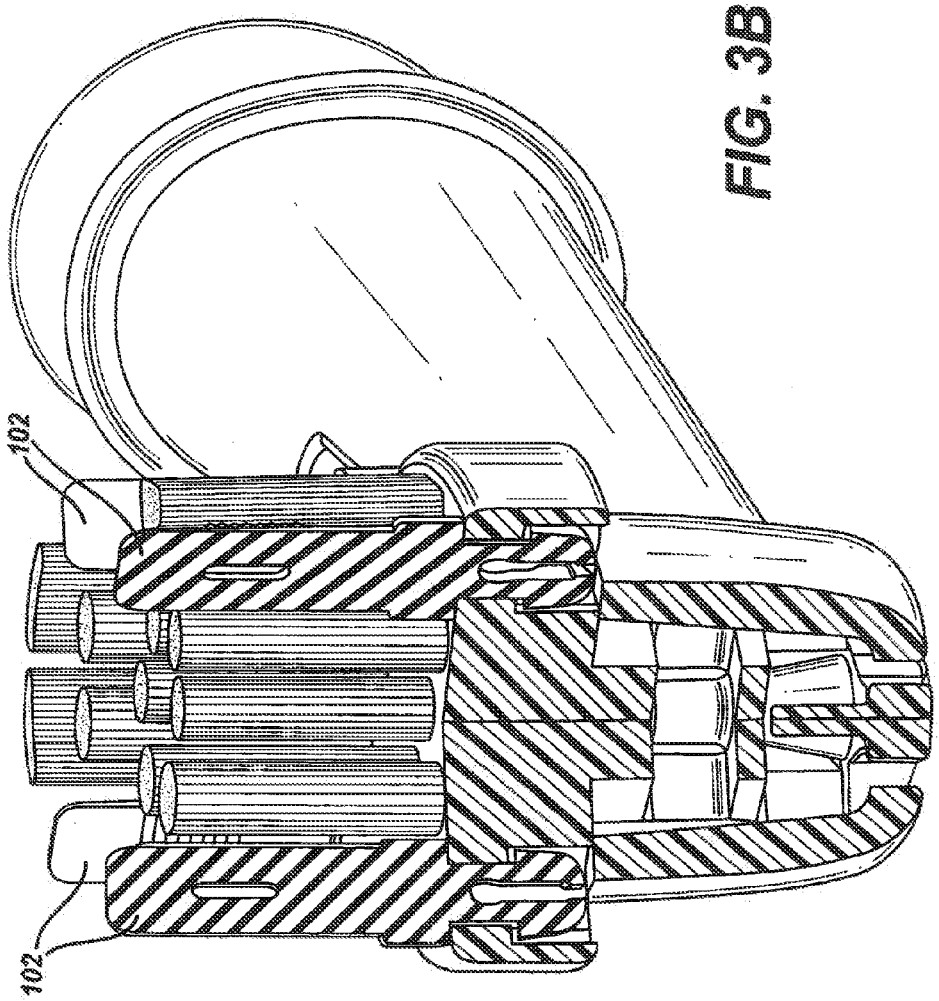

TOOTHBRUSHES

CROSS REFERENCE TO RELATED APPLICATION

This application is a continuation of U.S. application Ser. No. 10/666,497, filed on Sep. 19, 2003, now U.S. Pat. No. 7,941,886, the substance of which is incorporated by reference in its entirety herein.

FIELD OF THE INVENTION

This invention relates to toothbrushes, and more particularly to power toothbrushes.

BACKGROUND OF THE INVENTION

Power toothbrushes are well known and have been on the market for years. In typical power toothbrushes, tufts of bristles on the brush head extend generally perpendicularly from the top surface of the head. The head is oscillated, rotated and/or translated in order to provide enhanced tooth cleaning capability.

In many power toothbrushes, the top surface of the head is generally circular in shape, and is dimensioned to clean the larger teeth one at a time and smaller teeth two at a time, with most of the bristles typically contacting the tooth or teeth during brushing. In some power toothbrushes, the head has a generally oval shape.

SUMMARY OF THE INVENTION

In general, the invention features power toothbrush heads having particular arrangements of bristles and/or tufts of bristles, power toothbrushes including such heads, and methods of using such heads and toothbrushes.

In one aspect, the invention features a head for a power toothbrush including an elongated support member, and a plurality of bristles extending from the support member, at least some of the bristles having different heights, the bristles being arranged so that their heights are symmetric, in a non-translatable mirror image symmetry, about two planes of symmetry.

In another aspect, the invention features a head for a power toothbrush including an elongated support member, and a plurality of tufts of bristles extending from the support member, the tufts of bristles having at least three different heights, the tufts being arranged so that their tips define a rounded contour.

Some implementations of these aspects include one or more of the following features. The bristles or tufts have may different lengths, measured from a top surface of the support member. Alternatively, or in addition, the bristles or tufts may extend the same length from a top surface of the support member, and the top surface is contoured so that the bristles or tufts have different heights as measured from a horizontal plane taken through the lowest point on the top surface. The two planes of symmetry may be arranged about a central axis of the brush head. The bristles may be arranged in an may and tips of the bristles define a continuously curved surface. The two planes of symmetry may intersect in the vicinity of the center of the elliptical support member. The head may be configured for use on a power toothbrush having a rotationally oscillating motion. The tufts of bristles may have at least four different heights. The rounded contour may be lowest adjacent a pivot point of the head. A top surface of the support member may have an overall surface area of from about 170 to 200 mm$^2$. The head may further include one or more elastomeric element(s). The tufts may be arranged so that their heights are symmetric about two planes of symmetry. The height of the tallest bristles may be from about to 50% greater than the height of the shortest bristles. A top surface of the support member may have a length of about 14 to 19 mm, e.g., about 16 to 17 mm. The top surface may have a width of about 12 to 15 mm, e.g., about 13 to 14 mm. The top surface may have an aspect ratio (length/width) of about 1.2 to 1. The top surface may have a shape selected from the group consisting of oval, ellipse, rounded diamond, and rounded rectangle. The top surface may have a concave shape.

In a further aspect, the invention features a power toothbrush including a handle, and, extending from the handle, a head including an elongated support member, and a plurality of bristles extending from the support member, at least some of the bristles having different heights, the bristles being arranged so that their heights are symmetric, in a non-translatable mirror image symmetry, about two planes of symmetry.

In yet another aspect, the invention features a power toothbrush including a handle, and, extending from the handle, a head including an elongated support member, and a plurality of tufts of bristles extending from the support member, the tufts of bristles having at least three different heights, the tufts being arranged so that their tips define a rounded contour.

Some implementations of these aspects may include one or more of the features discussed above.

The invention also features, in another aspect, a head for a power toothbrush including an elongated support member, and a plurality of bristles extending from the support member, at least some of the bristles having different heights, the heights of the bristles being selected to provide a bristle tip contour that allows substantially all of the bristle tips to contact the dentition simultaneously during brushing.

In another aspect, the invention features methods of brushing teeth including contacting the teeth with bristles of one of the power toothbrushes discussed above.

In some implementations, the contour of the bristles or bristle tufts allows all or substantially all of the bristle tips to contact the dentition (tooth surface) when the toothbrush head is brushing one or more teeth of a user. Whether this occurs in a given implementation may be determined, e.g., by high speed videography. In some cases, the support surface from which the bristles extend is generally elongated, and the contour allows all of the bristle tips, including those at the distal ends of the head, to contact the dentition. As a result, a longer surface may be cleaned simultaneously, as compared to a flat brush having the same area or shape as projected onto a flat plane. Such brush heads also generally feel comfortable in the mouth, and do not seem overly bulky. A toothbrush that is contoured to match the general curvature of the dentition also holds the support surface at a more consistent position (i.e. height and angle) above the teeth. This allows taller cleaning elements to be incorporated into the toothbrush that are spaced appropriately to reach in between the teeth and other areas that are normally difficult to access.

The details of one or more embodiments of the invention are set forth in the accompanying drawings and the description below. Other features and advantages of the invention will be apparent from the description and drawings, and from the claims.

BRIEF DESCRIPTION OF THE DRAWINGS

FIG. 1 is a perspective view of a brush head according to one embodiment of the invention.

FIG. 1A is a side view of the brush head of FIG. 1.

FIG. 1C is a perspective view of a brush head similar to that shown in FIG. 1, except that the head is slightly tilted towards the handle, with planes of symmetry indicated.

FIG. 2 is a perspective view of a brush head according to an alternative embodiment.

FIG. 3 is a perspective view of a brush head according to another alternative embodiment.

FIG. 3A is a side view of the brush head of FIG. 3.

FIG. 3B shows the brush of FIG. 3 with a portion of the brush head cut away to show the pivoting mechanism.

DETAILED DESCRIPTION OF THE INVENTION

Figure 1B:
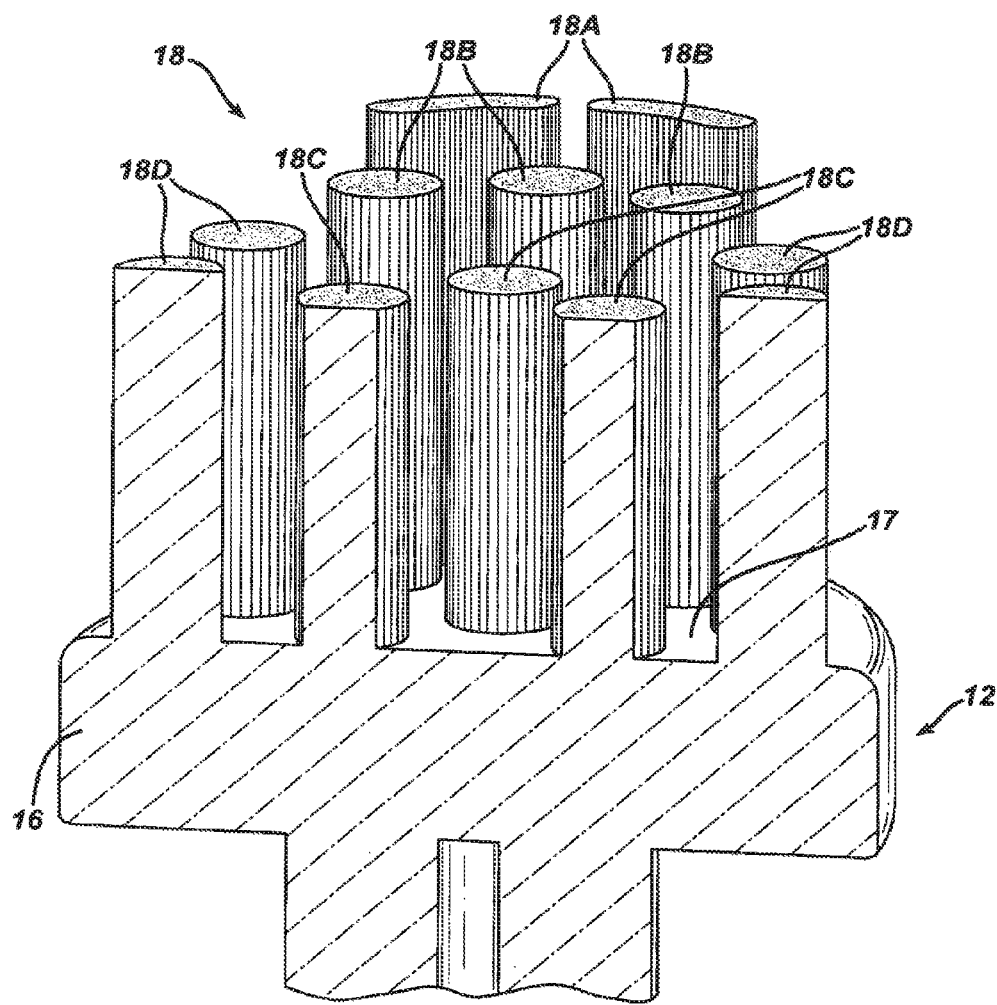
FIG. 1B is a transverse cut-away view of the brush head of FIG. 1.

Referring to FIG. 1, a power toothbrush 10 includes a head 12 and a neck 14. As is well known to those skilled in the art, head 12 is oscillated during brushing. Generally, the head 12 is oscillated in a rotating manner about an axis of rotation which typically extends through the center of the head but may be offset, as will be discussed below. An electric motor (not shown) oscillates the head through gearing, linkages, cranks, and/or other drive mechanisms as is well known. Electrical power may be supplied to the motor by rechargeable or primary (disposable) batteries. Further details as to how the head is oscillated will not be provided, as this aspect of the brush is not the focus of the invention.

Head 12 includes a generally elliptical support member 16 that is disposed approximately perpendicular to the axis of rotation of the head, and, extending from a top surface 17 of the support member 16, a plurality of bristle tufts 18. As will be discussed below, the top surface 17 typically is perpendicular to the axis of rotation, but may in some cases be tilted so that it is not perpendicular to the axis of rotation.

Although each tuft 18 is shown as a solid mass in the drawings, the tufts may each be made up of a great number of individual plastic bristles. The bristles may be made of any desired polymer, e.g., nylon 6.12 or 6.10, and may have any desired diameter, e.g., 4 to 8 mil. The tufts are supported at their bases by the support member, and may be held in place by any desired tufting technique as is well known in the art, e.g., by insert molding or a stapling process. The tufts may also be mounted to move on the support member, e.g., with a pivoting motion as will be discussed below with reference to FIGS. 2 and 3-3B.

The support member is generally elliptical, i.e., it has a long axis and a short axis. Preferably, the long axis has a length of about 14 to 19 mm, and the short axis has a length of about 12 to 15 mm. The ellipse may have an aspect ratio (long axis/short axis) of about 1.2 to 1. The head size is most preferably around 16 to 17 mm long by 13 to 14 mm wide. The overall surface area of the surface 17 of the support member is preferably about 170 to 200 mm$^2$ (0.270 to 0.305 sq in).

There is a height differential between the different bristle tufts. The curved, elongated interdental tufts 18A, i.e., the two tufts that are at each furthest edge of the support member, adjacent the long axis of the toothbrush neck 14 when the head 12 is at rest, are tallest. The round end tufts 18B that are immediately inboard of the interdental tufts 18A (three on each side) are the next tallest, followed by the side tufts 18D (three on each side), which are mounted along the edge of the support member between the two sets of round end tufts 18B. The shortest tufts are the inner tufts 18C, which are arranged in a ring of five tufts, inboard of the side and end tufts. The interdental tufts 18A may be, for example, about 20 to 50% taller than the inner tufts 18C, e.g., from about 7 to 8.5 mm in height, the end tufts 18B may be about 10 to 40% taller than the inner tufts 18C, e.g., about 6 to 8 mm in height, and the side tufts 18D may be, for example, about 0 to 25% taller than the inner tufts 18C, e.g., from about 5 to 7 mm in height.

Figure 1D:
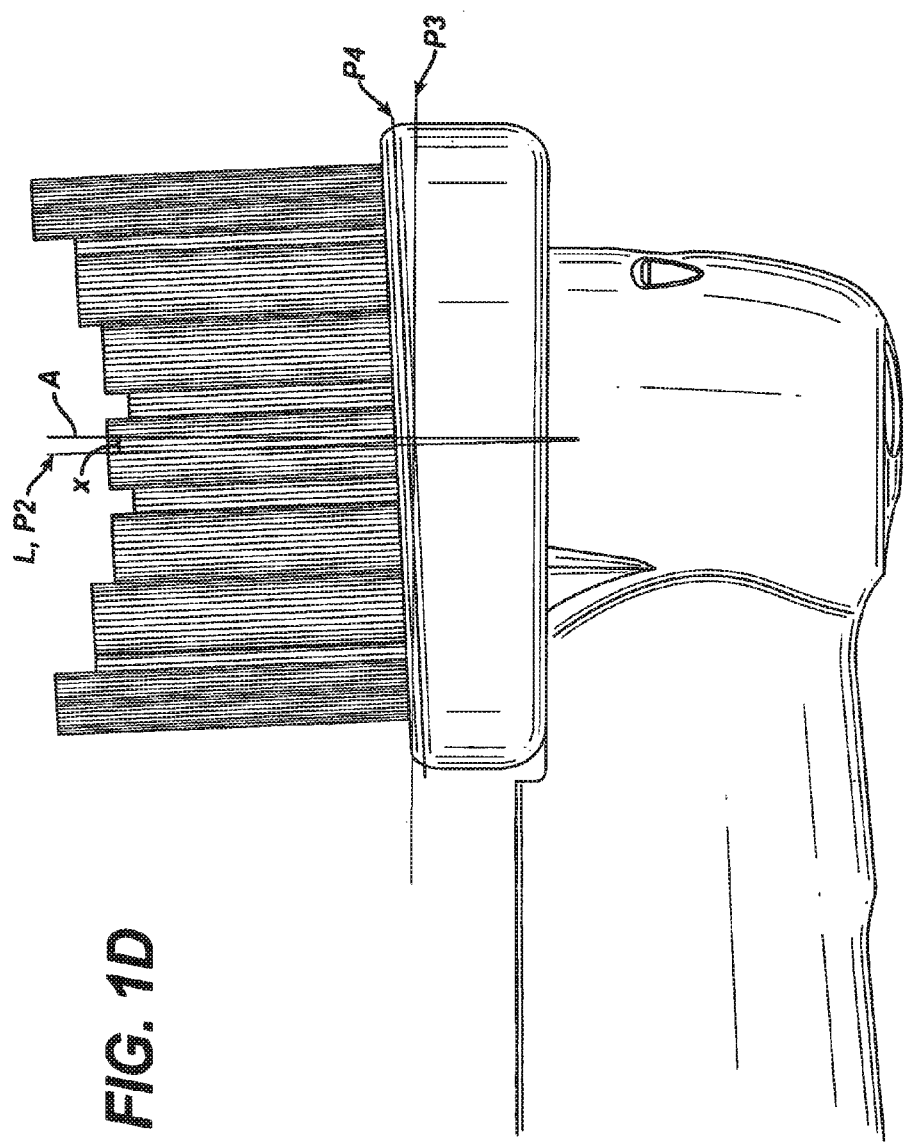
FIG. 1D is a side view of the brush head of FIG. 1C, with planes of symmetry indicated.

The contour produced by this height differential between the bristle tufts allows the tips of the bristles to conform closely to the shape of the dentition, allowing most or all of the bristles to contact the dentition during brushing of multiple teeth simultaneously. As shown in FIG. 1C, this contour is symmetric about two planes of symmetry, e.g., a plane (P1) taken through the long axis of the elliptical support member and a plane (P2) taken through the short axis of the support member. Both planes are perpendicular to the top surface 17 of the support member. It is noted that the line (L) defined by the intersection of these two planes (shown in FIG. 1D) may or may not be collinear with the axis of rotation (A) of the brush head. In the embodiment shown in FIGS. 1C and 1D, the axis of rotation A is perpendicular to a plane (P3) which is not parallel to or coplanar with the plane (P4) of the top surface 17 of the support member. The angle (X) between L and A is the result of the slight tilt of the brush head towards the handle, shown best in FIG. 1D. In other embodiments (e.g., the embodiment shown in FIGS. 1-1B), the axis of rotation A is perpendicular to plane P4.

The symmetry of the contour about planes P1 and P2 is a non-translatable mirror image symmetry, i.e., each quadrant is the mirror image of the two adjacent quadrants, but could not be "swapped" with either adjacent quadrant, i.e., "translated," without altering the contour defined by the tufts. Each quadrant can be rotated 180 degrees about the axis of symmetry defined by the intersection of planes P1 and P2 without altering the symmetry of the head, and each quadrant is a mirror image reflection of the adjacent quadrants. No quadrant can be translated without rotation, without altering the symmetry of the head.

As shown in FIG. 1B, in the embodiment shown in FIGS. 1-1B the top surface 17 of support member 16 is generally planar. As a result, the height differential is created by providing tufts of different lengths.

The brush head may include pivoting tufts. For example, brush 50, shown in FIG. 2, includes a head 51 that carries a plurality of fixed tufts 52 and a plurality of pivoting tufts 54. The tufts are arranged to define a contour similar to that described above. Techniques for providing pivoting tufts are described in U.S. Pat. No. 6,553,604, the disclosure of which is incorporated by reference herein. One type of pivoting mechanism is shown in FIG. 3B in the context of pivoting elastomeric elements.

The brush head may also include elastomeric elements, in addition to or instead of tufts of bristles. For example, as shown in FIGS. 3 and 3A a toothbrush 100 includes elastomeric fins 102 and tufts of bristles 104, arranged to define a contour as discussed above. The elastomeric elements are sized for interproximal insertion, to provide cleaning and massage of the interproximal areas, as described in U.S. Ser. No. 10/389,448, filed Mar. 14, 2003. In the embodiment shown in FIGS. 3-3B the elastomeric fins are pivotably mounted. However, the elastomeric elements may be stationary if desired, and the bristle tufts may be stationary or pivoting.

A number of embodiments of the invention have been described. Nevertheless, it will be understood that various modifications may be made without departing from the spirit and scope of the invention.

For example, while an elliptical support member has been shown and described above, the bristle contour described may be used with support members having other elongated shapes, e.g., oval, rounded diamond, or rounded rectangular.

Figure 4:
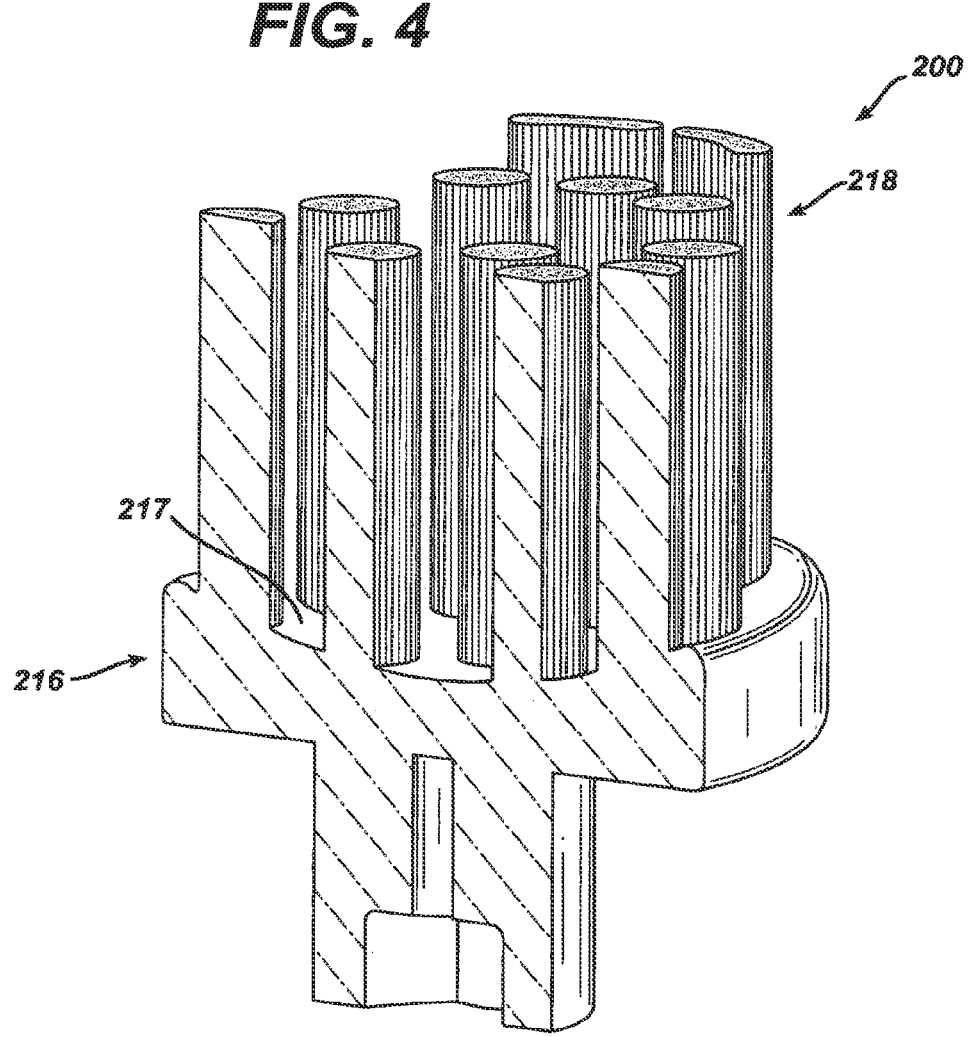
FIG. 4 is a transverse cut-away view of a brush head according to another alternative embodiment.

While, in the embodiments discussed above, the bristle height differential was determined by bristle length, in other embodiments the bristle height differential may be determined based on the geometry of the top surface of the support member. For example, as shown in FIG. 4, a brush head 200 includes a support member 216 having a concave top surface 217. In this embodiment, bristle tufts 218 are all of substantially the same length, but their heights define a contour similar to that described above due to the concave shape of the surface 217.

Moreover, while a brush head having four bristle heights is described above, other numbers of bristle heights may be used. For example, the bristle tufts may have three different heights, or five or more.

Alternatively, the bristles may be arranged in a uniform array, rather than tufts, and the height differential of their tips may define a continuously curved surface, e.g., a cup-shaped surface.

Additionally, while the contour shown in FIGS. 1-1A is symmetrical about two planes that intersect in the center of the surface 17 of the support member, symmetry could be defined about a point that is not centered on the support member.

While toothbrush heads having a plurality of elastomeric elements are shown in the figures and described above, some toothbrush heads may include a single elastomeric element. For example, the toothbrush head may include one of the elastomeric elements described in U.S. Ser. No. 10/364,148, filed Feb. 11, 2003, the disclosure of which is incorporated herein by reference.

Accordingly, other embodiments are within the scope of the following claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush head comprising:
    a neck having a long axis, the neck configured for releasable attachment to an electric toothbrush;
    an elliptical shaped support member having a top surface and a bottom surface;
    a drive mechanism for oscillating the support member; and
    a plurality of tufts that have different heights as measured from a horizontal plane taken through the lowest point on the top surface, the plurality of tufts including curved, elongated tufts extending from the top surface, the curved tufts being disposed at each furthest edge of the support member, end tufts extending from the top surface, the end tufts being disposed inboard of the curved tufts, side tufts extending from the top surface, the side tufts being disposed at the edge of the support member, and inner tufts arranged in a ring and extending from the top surface, the inner tufts being disposed inboard of the side tufts and the end tufts, such that the curved tufts are taller in height than the end tufts which are taller in height than the side tufts,
    wherein the support member includes a long axis and a short axis having an aspect ratio of about 1.2 to about 1.

2. A toothbrush head according to claim 1, wherein the side tufts are taller in height than the inner tufts.

3. A toothbrush head according to claim 1, wherein the tufts comprise a plurality of bristles, the bristles being arranged in an array such that their tips define a curved surface.

4. A toothbrush head according to claim 1, wherein the top surface has a concave shape.

5. A toothbrush head according to claim 1, wherein the curved elongated tufts are disposed adjacent the long axis of the neck.

6. A toothbrush head comprising:
    a neck configured for releasable attachment to an electric toothbrush;
    an elliptical shaped support having a top surface and a bottom surface, wherein the support member is elongated and includes a long axis and a short axis, a proximal end adjacent the neck and a distal end distal from the neck;
    a drive mechanism for oscillating the support member; and
    a plurality of tufts, the plurality of tufts including first and second sets of end tufts extending from the top surface, the first set of end tufts being disposed inboard of the proximal end of the support member and the second set being disposed inboard of the distal end of the support member; a first and second set of side tufts extending from the top surface, the first set of side tufts being disposed directly opposite the second set of side tufts along an edge of the support member; inner tufts arranged in a ring and extending from the top surface, the inner tufts being disposed inboard of the side tufts and the end tufts; and at least four elastomeric elements circumferentially spaced on the edge of the support member, each elastomeric element being disposed adjacent at least one of the side tufts
    wherein the support member has an aspect ratio of about 1.2 to about 1.

7. A toothbrush head according to claim 6, wherein the elastomeric elements are stationary.

* * * * *